(12) United States Patent
Skarstad et al.

(10) Patent No.: US 7,867,702 B2
(45) Date of Patent: Jan. 11, 2011

(54) SCREEN FOR NOVEL PROTEIN INHIBITORS BASED UPON ENGINEERED CELL LINE CONTAINING AN INDUCIBLE OVERACTIVITY GENE AND COMPENSATORY GENE

(76) Inventors: Kirsten Skarstad, c/o Department of Cell Biology, Institute for Cancer Research, The Norwegian Radium Hospital, N-0310, Oslo (NO); Solveig Fossum, 3100 N St., #5, NW., Washington, DC (US) 20007; Walter Messer, Hammerstr. 45D, 14167, Berlin (DE); Christoph Weigel, Kaiserdamm 17, 14057, Berlin (DE)

( * ) Notice: Subject to any disclaimer, the term of this patent is extended or adjusted under 35 U.S.C. 154(b) by 907 days.

(21) Appl. No.: 10/559,244

(22) PCT Filed: Jun. 3, 2004

(86) PCT No.: PCT/GB2004/002347
§ 371 (c)(1),
(2), (4) Date: Jun. 26, 2006

(87) PCT Pub. No.: WO2004/108958
PCT Pub. Date: Dec. 16, 2004

(65) Prior Publication Data
US 2007/0009890 A1    Jan. 11, 2007

(30) Foreign Application Priority Data
Jun. 5, 2003    (GB) .................................. 0312972.3

(51) Int. Cl.
*C12Q 1/68*    (2006.01)
*C12N 1/21*    (2006.01)

(52) U.S. Cl. ...................................... 435/6; 435/252.33
(58) Field of Classification Search ...................... None
See application file for complete search history.

(56) References Cited

U.S. PATENT DOCUMENTS

| 2002/0022718 A1 | 2/2002 | Forsyth et al. |
| 2002/0045592 A1 | 4/2002 | Zyskind et al. |

FOREIGN PATENT DOCUMENTS

| WO | WO 97/43727 | 12/1997 |

OTHER PUBLICATIONS

Boye, E. et al. (2000) "Limiting DNA replication to once and only once" EMBO Reports 1:479-483.
Erzberger, J.P. et al. (2002) "The structure of bacterial DnaA: implications for general mechanisms underly8ing DNA replication initiation" The EMBO Journal 21:4763-4773.
Giraldo, R. et al. (2001) "Similarities between the dna replication initiators of gram-negative bacteria plasmids (RepA) and eukaryotes (Orc4p)/archaea (Cdc6p)" PNAS 98:4938-4943.

Hansen, F. et al. (1995) "Initiation of chromosome replication after induction of DnaA protein synthesis in a dnaA(null) rnh mutant of *Escherichia coli*" Molecular Microbiology 15:149-154.
Hansen, F.G. et al. (1992) "Cloning and nucleotide sequence determination of twelve mutant dnaA genes of *Escherichia coli*" Mol. Gen. Genet. 234:14-21.
Hirota, Y. et al. (1970) "On the process of cellular division in *Escherichia coli*. III. Thermosensitive mutants of *Escherichia coli* altered in the process of dna initiation" J. Mol. Biol. 53:369-387.
Itaya, M. et al. (1991) "Correlation of activity with phenotypes of *Escherichia coli* partial function mutants of rnh, the gene encoding RNase H" Mol. Gen. Genet. 227:433-437.
Katayama, T. (2001) "Feedback controls restrain the initiation of *Escherichia coli* chromosomal replication" Molecular Microbiology 41:9-17.
Katayama, T. et al. (1994) "Hyperactive initiation of chromosomal replication in vivo and in vitro by a mutant initiator protein, DnaAcos, of *Escherichia coli*" Journal of Biological Chemistry 269:12698-12703.
Katayama, T. et al. (1995) "Characterization of *Escherichia coli* DnaAcos protein in replication systems reconstituted with highly purified proteins" Molecular Microbiology 18:813-820.
Katayama, T., et al. (1997) "CedA is a novel *Escherichia coli* protein that activates the cell division inhibited by chromosomal dna over-replication" Molecular Microbiology 26:687-697.
Kellenberger-Gujer, G. et al. (1978) "A cold sensitive dnaA mutant of *E. coli* which overinitiates chromosome replication at low temperature" Molec. Gen. Genet. 162:9-16.
Kogoma, T. et al. (1983) "The origin of replication, oriC, and the dnaA protein are dispensable in stable DNA replication (sdrA) mutants of *Escherichia coli* K-12" The EMBO Journal 2:463-468.
Kohiyama, M. (1968) "DNA synthesis in temperature sensitive mutants of *Escherichia coli*" Cold Spring Harb. Symp. Quant. Biol. 33:317-324.
Liang, C. et al. (1995) "ORC and Cdc6p interact and determine the frequency of initiation of dna replication in the genome" Cell 81:667-676.
Liang, C. et al. (1997) "Persistent initiation of DNA replication and chromatin-bound MCM proteins during the dell cycle in cdc6 mutants" Genes & Development 11:3375-3386.

(Continued)

*Primary Examiner*—Nancy Vogel
(74) *Attorney, Agent, or Firm*—Knobbe Martens Olson & Bear LLP (57) ABSTRACT

The present invention provides a method for identifying the presence of a protein inhibitor of a target protein in a sample, comprising the steps of a) contacting said sample with a cell, wherein said cell contains i) an inducible lethal overactivity mutation in a gene affecting the target protein; and ii) a mutation in a second gene, wherein the activity of the target protein is essential to the cell and the mutation in the second gene functionally compensates for any reduction in the activity of the target protein; b) inducing the lethal overactivity mutation; and subsequently c) assessing protein inhibition by comparing the degree of survival of the cell in the presence and the absence of said sample. Also provided are cells for use in said method.

2 Claims, 4 Drawing Sheets

OTHER PUBLICATIONS

Liu, J. et al. (2000) "Structure and function of Cdc6/Cdc18: implications for origin recognition and checkpoint control" Molecular Cell 6:637-648.

Muzi-Falconi, M. et al. (1996) "cdc18+ regulates initiation of dna replication in schizosaccharomyces pombe" PNAS USA 93:1566-1570.

Nishitani, H. et al. (1995) "p65$^{cdc18}$ plays a major role controlling the initiation of dna replication in fission yeast" Cell 83:397-405.

Sekimizu, K. et al. (1987) "ATP activates dnaA protein in initiating replication of plasmids bearing the origin of the *E. coli* chromosome" Cell 50:259-265.

Shinpuku, T. et al. (1995) "Phenotypes of dnA mutants of *Escherichia coli* sensitive to detergents and organic solvents" Biochemical and Biophysical Research Communications 212:84-89.

Shrager, J. et al. (2001) "High throughput discovery: search and interpretation on the path to new drugs" In K. Crowley, et al. (Eds.) Design for Science. Hillsdale, NJ: Lawrence Erlbaum, pp. 325-348.

Skarstad, K. et al. (1994) "The initiator protein DnaA: evolution, properties and function" Biochimica et Biophysical Acta 1217:111-130.

Von Meyenburg, K. et al. (1987) "Mode of initiation of constitutive stable dna replication in RNase h-defective mutants of *Escherichia coli* K-12" J. of Bacteriology 169:2650-2658.

Wei, M.H. (2000) "Discovery of novel antibiotics: application of structural and functional genomics" http://bioinfo.mbb.yale.edu/mbb452a/2000/projects/Marlynn-H-Wei.html.

Weigel, C. et al. (1999) "The n-terminus promotes oligomerization of the *Escherichia coli* initiator protein DnaA" Molecular Microbiology 24:53-66.

Itaya, M. et al. 1999 "Isolation of RNase H genes that are essential for growth of *Bacillus subtilis* 168" *J Bacteriol* 181:2118-2123.

Kato, J and Katayama, T. 2001 "Hda, a novel DnaA-related protein, regulates the replication cycle in *Escherichia coli*" *The EMBO J* 20:4253-4262.

Ogawa, T, et al. 1984 "RNase H confers specificity in the dnaA-dependent initiation of replication at the unique origin of *Escherichia coli* chromosome in vivo and in vitro" *Proc Natl Acad Sci USA* 81:1040-1044.

Von Meyenburg, K et al. 1987 "Mode of initiation of constitutive stable DNA replication in RNase H-defective mutants of *Escherichia coli* K-12" *J Bacteriol* 169:2650-2658.

SCREEN FOR NOVEL PROTEIN INHIBITORS BASED UPON ENGINEERED CELL LINE CONTAINING AN INDUCIBLE OVERACTIVITY GENE AND COMPENSATORY GENE

RELATED APPLICATIONS

This application is a U.S. National Phase of International patent application No. PCT/GB2004/002347, filed Jun. 3, 2004, designating the United States of America and published in English on Dec. 16, 2004 as WO 2004/108958, which claims the benefit of priority of British patent application No.: 0312972.3, filed Jun. 5, 2003.

FIELD OF THE INVENTION

The present invention relates to methods of identifying novel protein inhibitors (preferably antibiotics) by means of an assay using cells which contain mutations affecting two separate genes. The first mutation is an inducible (or conditional) lethal overactivity mutation, preferably causing over-initiation of DNA replication. Protein inhibitors are identified by their ability to inhibit the function (e.g. activity) of the gene product encoded by the lethal overactivity mutation, thereby overcoming the lethal overactivity characteristic of the cell. The second mutation increases the sensitivity of the assay by providing an alternative/compensating mechanism e.g. an alternative DNA initiation pathway, thereby allowing the cell to survive if the protein inhibitor is sufficiently potent to strongly inhibit the function (e.g. activity) of the gene product encoded by the lethal overactivity mutation to levels at which the cell cannot survive. Cells, particularly bacteria, for use in the assay are also provided.

BACKGROUND OF THE INVENTION

Protein inhibitors, which may function in different ways to "inhibit" a protein (e.g. by inhibiting its synthesis or its activity), are widely used as drugs to combat diseases. The diseases may be caused by overexpression or overactivity of the protein in question, as in the case in a number of cancers where the overexpression of certain oncogenes is involved with the development of malignancies e.g. HER2/neu in breast cancer, the ras oncogene and the myc oncogene. The overexpression may cause overactivity, or overactivity may result from mutation. Oncogene proteins are frequently components of a pathway, such as a signalling pathway, that is important in the regulation of cell growth. Once a protein is shown to be required for the cause or progress of a disease state, it is desirable to "target" the protein and attempt to find drugs that act to prevent the disease-related function of the protein.

The disease may also be an infection, such as a fungal or bacterial infection. Such diseases may be combatted with antibiotics, which again act to inhibit the function of a "target" protein as infection introduces new proteins into the infected cells. These proteins that are not found in the uninfected host cell may be target proteins.

Infectious diseases are a major cause of mortality worldwide and as such, new agents that are useful to act against infection are required. However, the overuse of antibiotics in particular has led to the phenomenon of antibiotic resistance where antibiotics become ineffective against microorganisms and it is therefore of crucial importance to develop new and improved antibiotics. It is particularly important to identify antibiotics that are chemically distinct from those that are currently used. Microorganisms that exhibit antibiotic resistance to a certain antibiotic are more likely to show resistance to one that is chemically related, than one which is structurally and functionally distinct. Therefore, new antimicrobial compounds that are identified based on their function, rather than their structure, may be of particular use. The development of antibiotics that act against targets for which no known antibiotics exist is also of particular interest.

Current antibiotic targets include enzymes involved in protein synthesis and membrane transporters or cell wall components. These targets are currently identified in a number of ways. The huge increases in nucleic acid sequence data that is available has led to an increase in the ability to attribute a function to a protein based on the comparison of sequence data. The sheer amount of data available however makes this difficult and about 25-40% of the genes in a bacterial genome will not have matches with counterpart, known genes (Smith D. R. (1996) Trends Biotechnology 8: 290-3). In addition, the fact that two genes share sequence homology does not always mean that they will be structurally similar.

Drug targets, whether for antibiotics or against other diseases, should ideally have the following properties: they must be necessary for the pathogen or disease to survive, grow or act; in relation to antibiotic targets, or anti-pathogenic targets it is also useful that the target protein is absent or distinct in humans, or the mammal which is to be treated; and the degree of conservation of structure of the drug target between species that are being combatted is preferably high. To date, no drugs that target the DNA replication machinery have been identified.

Once a target protein has been identified, it is necessary to identify compounds that may act to inhibit or impede its function, whether in a disease state or in the pathogen. The process of screening for inhibitory compounds, which previously has been labourious and time consuming has been improved by technologies that allow high throughput screening where many hundreds or even thousands of compounds may be tested simultaneously or in parallel.

In general, such screens to identify antibiotics or other protein inhibitors are "negative" screens. In these screens, a protein inhibitor is identified following the application of a test substance to a cell population, when the cell population exhibits a reduction in viability. This follows from the fact that one of the properties of the target outlined above is that it is essential to the continuing growth and proliferation of the pathogen in question. Interfering with this essential function affects cell viability. Thus, most screening techniques rely on a negative result ensuing from the abrogation of function of the target, such as the death or reduction in growth of cells containing and requiring it. This approach suffers from several disadvantages. Several different assays must be performed, sequentially or in parallel, to ensure that the observed effect on cell viability is specific to the target protein. The fact that the effect, e.g. cell death alone is seen is not sufficient to confirm that the effect is caused by an effect on the target protein. The test substance may have affected a different target protein or the effect may be a general effect that is entirely unrelated to the specific target protein. Thus, such negative screens are time consuming and it is not possible to obtain a result without performing multiple assays.

It would be advantageous to have an assay or screen for protein inhibitors that depends on a positive result or outcome, such as increased cell growth or survival of a mutant cell that is unable to grow otherwise. Such positive screens are advantageous as they avoid many of the problems associated with negative screens, such as high background levels of cell death or lack of growth that may not be attributable to the specific action of a potential inhibitor, but may be due to other reasons. No such positive screens are presently known in the art. The present invention now provides such a test.

Lethal overactivity mutants are mutants that contain mutation(s) such that the activity of a particular gene product produced or expressed is greater, compared to the wild-type organism or the "non-mutated" gene product (i.e. the gene product prior to the introduction of the lethal over-activity mutation—it is not precluded that the gene product may carry other mutations not related to the lethal overactivity). This may be due to differences in the activity of the gene product itself, in its levels of expression or production, or in the regulation of its activity (e.g. due to an increase or decrease in the expression and/or activity of a regulatory molecule). Thus a lethal overactivity mutant may be viewed as one in which the "functionality" of the gene product concerned is increased. The increase in activity (or "functionality") of this gene product is detrimental to the survival and/or growth of the mutant cell. The gene product may thus be any product which is lethal, or which has a significant negative effect on the growth and/or survival of the organism, when its activity exceeds certain levels (e.g. "normal" levels e.g. prior to the mutation, or native or wild-type levels) e.g. when it is "overactive". Such over-activity may, as mentioned above, be achieved in various ways, including by an increase in amount or content, or levels of the gene product e.g. due to increased expression or reduced breakdown, or by increased or prolonged activity. Such mutants are therefore useful in positive screens. However such mutations are rare in nature and can be difficult to generate.

DnaA is an eubacterial protein that initiates chromosomal replication in bacteria (Kornberg and Baker 1992, DNA replication, W.H. Freeman). It is at this stage that the cycle of chromosomal replication is regulated. DNA replication is also dependent on the presence of a unique chromosomal sequence, OriC the replication origin. Both OriC and DnaA are required for successful initiation of replication, and these two components form a nucleoprotein complex. About 20-40 monomers of DnaA protein are present in the OriC-DnaA complex, ATP-bound DnaA causes the DNA duplex to start to unwind, thus allowing the DnaB helicase to extend the unwinding, prior to synthesis of the complementary strands by DNA polymerase III holoenzyme (Skarstad and Boye, Biochim. Biophys. Acta, 1994, 1217, 111-130, reviewed in Katayama et al., Molecular Microbiology, 2001, 41(1), 9-17).

Initiation of DNA replication in prokaryotes and eukaryotes is highly regulated by a number of mechanisms, due to its importance in the cell cycle. Excessive initiation events eventually lead to cell death.

One example of a mutation that causes hyperactive initiation is DnaAcos, which is a mutation identified in *E. coli* (Kellenberger-Gujer et al., Molec. Gen. Genet. 162, 9-16, 1978; and Katayama et al. (1994), Journal of Biological Chemistry, 269(17), 12698-12703). This mutant was isolated as a temperature resistant suppressor from a temperature sensitive DnaAts46 mutant. DnaAts46 is a well-characterised *E. coli* mutant which expresses a DnaA protein which is inactive at elevated temperatures (42° C.), resulting in a mutant strain which is unable to initiate replication at elevated temperatures (Kohiyama, Cold Spr. Harb. Symp. Quant. Biol. 33, 312-324 (1968); Hirota et al., J. Molec. Biol. 53, 369-387 (1970).

The DnaAcos mutant is known to have the following properties. Firstly, its growth is cold sensitive; it grows normally at 42° C., however replication of chromosomal DNA over-initiates immediately once the cells are shifted to grow at the restrictive temperature of 30° C. DnaAcos has been identified as a suppressor mutant of dnaAts46 i.e. it suppresses the dnaAts46 phenotype and represents an intragenic suppressor mutant. The suppressor mutations (Q156L and Y271H) result from base substitutions in the dnaA gene (Hansen et al., 1992, Mol. Gen. Gent., 234, 15-21, Skarstad and Boye, 1994, Biochim Biophys Acta, 1217, 111-130, Kellenbergen-Gujer et al., 1978, Mol. Gen. Genet., 162, 9-16).

The cold sensitivity of dnaAcos is dominant over the wild-type dnaA allele, and the over-initiation seen at the restrictive temperature is independent of de novo protein synthesis. Interestingly, there is no increase in the amount of DnaA protein in this mutant and the mutant phenotype is thought to depend on increased and/or prolonged DnaA activity. Since initiation with the mutant occurs repeatedly it has been suggested that somehow the initiation competence of the mutant DnaAcos protein is sustained, e.g. through a conformational change.

The mechanism of over-initiation in the mutant is not fully understood, although the DnaAcos protein has been purified and characterised in vitro (Katayama et al., 1995, Mol. Microbiol., 18, 813-820). It sustains affinity to a DnaA-binding sequence and functions in the loading of DnaB helicase onto single-stranded DNA. The purified wild type DnaA protein binds ATP and ADP. However, the DnaAcos protein is unable to bind nucleotide. Wild type ATP-DnaA is active in initiation of replication while wild-type ADP-DnaA is inactive (Sekimizu et al., 1987, Cell, 50, 259-265). The hydrolysis of wild-type ATP-DnaA to ADP-DnaA inactivates DnaA to regulate its function and this occurs as soon as replication forks are underway to prevent reinitiation of an already initiated origin (Boye et al., 2000, EMBO Rep. 1, 479-483). The DnaAcos protein seems to be an "unregulated" form of DnaA protein that is always "turned on" and therefore causes excess DNA replication at lower temperatures (30° C.). At higher temperatures (42° C.) the protein is apparently partially inactive, explaining that the over-initiation is reduced compared to the restrictive temperature, and the cells therefore survive.

Other DnaA mutants have been, or may be, developed which are similar to, or have the properties of DnaAcos (e.g. which exhibit temperature sensitive replication) e.g. over-inhibition of replication at lower temperature (e.g. 30° C.). One such mutant is DnaA219 used in the Examples herein.

DnaA and homologues of this protein in other prokaryotes or in eukaryotes or Archaea, represent an example of a target for a protein inhibitor, as it is an essential protein for *E. coli* and is also highly conserved between different bacterial species. Other DNA replication initiator proteins (whether eukaryotic, prokaryotic or archael) may also represent protein inhibitor targets.

In a comparison of 104 sequences from 96 species, DnaA was shown to have a highly conserved primary sequence, and the overall arrangement of 15 α helices and 9 β strands seen is over 93% of the sequences (Weigel and Messer 2002, on the World-Wide Web at molgen.mpg.de/~messer). Furthermore, the Cdc6 and Orc initiator proteins of yeast, e.g. *Saccharomyces cerevisiae* shows striking structural similarity to DnaA and thus represent a eukaryotic target protein (Erzberger et al. (2002) EMBO J 21: 4763-73, Liu et al., (2000) Mol. Cell. 6: 637-48).

Overactivity mutants of target proteins, e.g. DnaA mutants that over-initiate DNA replication, can be used to assay for potential new protein inhibitors; any protein inhibitor that interferes with the function of the target protein (e.g. DnaA) will reduce the amount of over-initiation and thereby increase the growth of the population of mutant cells compared to their growth in the absence of such a protein inhibitor. However such an assay would only allow the detection of weak protein inhibitors i.e. those that only reduce DnaA activity, to normal or near normal levels (i.e. to levels comparable to wild-type DnaA activity or to activity of the DnaA protein prior to introduction of the lethal overactivity ("cos") mutation (i.e. the "source" or "origin" or "parental" protein into which the lethal overactivity mutation is introduced)), such that there is sufficient DnaA activity for the cells to survive but the DnaA activity is not high enough to cause over-initiation, that leads to the death of the cells. It can be seen that such a screen would not allow a distinction to be made between the presence in the sample of a strong protein inhibitor which would severely reduce target protein, e.g. DnaA levels and cause cells to die due to lack of initiation of DNA replication, and the absence in the sample of any inhibitor, which causes the cells to die due to over-initiation. An analogous situation can be envisaged for other target proteins, and their lethal-overactivity mutants.

As used herein "mutation" refers to the changes in nucleotide sequence and "mutant" refers to the gene or gene product, or cell containing such a mutation.

Thus, even when a mutation is identified that enables the use of a "positive" screen i.e. a screen whereby the presence of a protein inhibitor is indicated by an increase in cell viability, rather than a decrease, it can be seen that such screens are not always suitable to identify protein inhibitors over a full range of potency. The relative rarity of lethal overactivity mutants which cause cell death by virtue of their increased activity, such as DnaAcos (or analogous over-activity mutations in other DNA replication initiator proteins), in combination with this fact, means that it was not immediately apparent, or straightforward, how to devise an effective positive screen for protein inhibitors.

To increase the efficacy of this type of screen and hence the range of inhibitors that may be identified, the present inventors have identified a mechanism whereby the use of a second mutation in the cell containing the first (i.e. lethal overactivity) mutation compensates for any severe reduction in activity of the target lethal over-activity mutation protein that may be caused by the presence of a strong protein inhibitor in a test sample. This second mutation does not affect normal cell growth or the lethal overactivity of the first mutation, however its presence compensates for any severe reduction in activity of the target protein caused by the presence of a strong protein inhibitor in the test sample. The second mutation thus salvages, or rescues, the test strain from a severe or total reduction of activity in the target protein. In this way, the inventors have been able to achieve a reliable and effective positive screen or assay for a protein inhibitor.

The rnh gene of *E. coli* encodes RNaseH. This enzyme functions to cleave and thereby degrade RNA in DNA:RNA hybrids. Thus, a cell containing a functional inactivation of rnh through e.g. mutation or deletion of the gene will contain persisting RNA:DNA hybrids, and the presence of such hybrids permits initiation of replication to occur independently of DnaA, and independently of the chromosomal origin OriC. Initiation of replication thus occurs from these RNA:DNA hybrids, which do not persist in cells that contain a functional RNaseH enzyme. In this way, initiation of replication does not require OriC or DnaA, and proceeds in the absence of a fully active wild-type initiation system. For example, partially functional rnh mutants are known to permit the growth of mutants that are incapable of using OriC, (Taya and Crouch, 1991, Mol. Gen. Genet., 227: 433-437; Kogoma and von Meyenburg, 1983, EMBO J. 2: 463-8).

The combination of the two mutations, DnaAcos and a deletion in rnh in *E. coli* (or indeed in other organisms) has not been achieved previously.

In order for cells (e.g. a population of cells) containing these two mutations to be propagated, the lethal overactivity mutant should be "inducible" i.e. capable of being "turned on" or "switched on" or expressed in particular conditions only, such that its expression may be controlled, or the phenotype is only seen when in the induced state. The cells are cultured (e.g. the cell population is expanded and maintained in culture) under conditions whereby the lethal overactivity is not induced. The assay is then performed under conditions whereby the lethal overactivity is induced. This may for example require that the mutated gene is placed under the control of an inducible promoter or the mutation may be a temperature or cold sensitive mutation, such as DnaAcos, or other conditional mutation.

Prior art methods are thus lacking that describe positive screens for protein inhibitors and antibiotics, and that allow detection of a full range of inhibitors.

SUMMARY OF THE INVENTION

Thus in one aspect, the invention provides a method for identifying a protein inhibitor of a target protein, preferably a specific protein inhibitor, (e.g. identifying the presence of a protein inhibitor in a test sample) said method comprising the steps of:

a) contacting said inhibitor (or test sample containing said inhibitor) with a cell (e.g. a cell population), wherein said cell (e.g. cell population) contains an inducible lethal overactivity mutation in a gene affecting (e.g. the gene encoding) the target protein (the "first gene") and a mutation in a second gene, wherein the activity of the target protein is essential to the cell, and the mutation in the second gene functionally compensates for any reduction in the activity of the first gene product (e.g. target protein);

b) inducing the lethal overactivity mutation; and subsequently c) assessing protein inhibition by comparing the degree of survival of the cell (e.g. cell population) in the presence and the absence of said inhibitor (or test sample).

The method of the invention can thus be seen to provide an assay for protein inhibitors e.g. novel protein inhibitors, of a desired target protein. The method can thus be used to screen for (or as a screen for) novel protein inhibitors (which includes both novel compounds or entities, or to identify, or screen for, a novel protein inhibitor activity of existing or known compounds or entities).

By "protein inhibitor" it is meant any compound or entity that is able to prevent or reduce the normal function of the target protein, and includes all entities or substances that are capable of directly or indirectly diminishing the function of the protein. This may be achieved by affecting the transcription, translation, post-translational modification, activity or regulation of activity of the protein. Preferably the activity of the protein is affected, and more particularly, the target protein is a functional protein which exhibits a particular activity (e.g. which mediates its function). Thus, the target protein may be an enzyme or a binding protein and the inhibition may be achieved by inhibiting the enzymatic or binding activity of the target protein. This may be achieved directly by interacting and/or interfering with the active site of the enzyme or the binding site of the binding protein, or another site on the protein, by interfering with or preventing the correct folding of the protein such that it is not able to function e.g. it cannot recognise its substrate or binding partner or key amino acid residues involved in the chemical or binding reactions are not correctly configured. A "binding protein" may be any protein which is capable of binding a molecule or substance in a cell (i.e. any cellular entity). Preferably the binding protein is capable of specifically binding such a cellular entity. The binding protein may exert a functional effect by, or through, the binding (e.g. a functional effect mediated by the binding) or it may bind a functional entity (i.e. an entity which carries out a function in a cell). Analogously, the target protein may be any kind of effector protein, which has a functional effect in the cell e.g. by interacting with another component in the cell and the protein inhibitor may inhibit the functional effect of that protein.

The inhibition may result in less than 70%, 60%, 50%, 40%, 30%, 20%, 10%, 5%, 2% or 1% of normal activity. Preferably the activity is completely abrogated and no residual protein activity remains.

The "target protein" may be any protein that is essential to the cell. More particularly, the target protein may be any protein that is essential to the growth and/or survival of the cell. It may thus be a protein associated with a vital cellular process, e.g. a cellular process essential to the growth and/or survival of the cell. It will be understood in this regard that such a protein would be essential to that process. For example, the target protein may be a protein associated with or involved in a biosynthesis process or reaction, e.g. synthesis of a cellular product or biological molecule or intermediate, including for example synthesis of nucleic acids (including all forms of DNA and RNA that may occur in cells) and proteins, as well as other molecules which may occur in cells. A target protein may thus be involved in the replication of DNA (DNA synthesis), synthesis of RNA (e.g. transcription of DNA into mRNA, translation of mRNA and synthesis of proteins, as well as in other cellular or biological reactions or processes. The target protein may be a protein associated with the initiation of any such a cellular process or reaction, e.g. an initiator of DNA replication or of protein synthesis. DNA replication initiator proteins are preferred, particularly such DNA replication initiator proteins in prokaryotes, particularly bacteria, and especially in *E. coli*.

In such a case, the lethal over-activity mutation in the first gene thus results in increased DNA replication, and in particular increased DNA replication at a lethal level. The second mutation compensates for reduction in or loss of DNA replication activity (due to inhibition by the protein-inhibitor undertest by providing an alternative mechanism or route for DNA replication (i.e. the second mutation results in increased DNA replication, or in DNA replication that would not occur in the absence of the second mutation).

The inhibition is not measured directly, but rather is measured functionally, in that it releases the mutant cell of the assay from the effect of the lethal overactivity mutation on its survival and/or growth. The inhibition of the target protein can therefore be measured by assessing (e.g. measuring) the cell population numbers. A positive result i.e. the presence of a protein inhibitor is indicated by a measurable or detectable increase in cell growth e.g. a statistically significant increase in cell growth, for example at least a tenfold, twenty-fold, thirty-fold, fifty-fold or a hundred-fold increase in cell growth, for example as measured by appropriate means e.g. spectrophotometrically by determining an increase in absorbance of the cell culture (e.g. growth medium) or increase in optical density e.g. $OD_{450}$ or other spectrophotometric or calorimetric assays for proteins or other cell components. Growth may be detected in any convenient or desired way. Thus, by way of further example, cell (e.g. bacterial) colonies may be counted or otherwise enumerated.

By "specific" protein inhibitor it is meant that the inhibitor acts only, or preferentially or selectively on the protein or class of proteins affected by the lethal overactivity mutation, and does not affect the function of other structurally or functionally unrelated proteins or classes of proteins. Thus "specific" may be seen to refer to the species from which the target protein is derived, or to the class of proteins. A specific inhibitor is thus able to distinguish between different proteins and will only be detected in the assay if the function of the protein affected by the lethal overactivity mutation is inhibited. The specific protein inhibitor will preferably reduce the activity or the function of the protein.

The protein inhibitor may be another protein, or a peptide, a small molecule e.g. a small organic molecule, antibody, ribozyme, antisense RNA or DNA, or an analogue of the substrate etc. The protein inhibitor may thus be any chemical entity. Preferably the protein inhibitor is an antibiotic. The antibiotic may be naturally derived or synthetic and may be a derivative or chemically synthesised variant of a naturally derived antibiotic.

"Contacting" as used herein refers to providing suitable contact between the inhibitor (or test sample) and the cell (e.g. cell population) so as to allow the inhibitor (or components of the test sample) to enter the cells (e.g. permeate the cell membrane and/or the cell wall) and interact and/or interfere directly or indirectly with the target protein. Thus, the inhibitor/test sample may simply be brought into contact with the cell(s) for example by adding it to the cells or to a medium containing the cell(s) e.g. a culture medium or culture of the cells. Conveniently, the cells may be grown (or cultured or maintained) in a liquid medium to which the inhibitor/test sample is introduced or added. Alternatively, the cells may be contained in or on a solid medium (e.g. a culture dish or vessel or plate) to which the inhibitor/test sample is introduced or added.

The "test sample" applied to the cell may be any sample, for example any sample consisting of or containing the test inhibitor substance (i.e. the protein inhibitor to be tested), e.g. a pure sample, or may represent a pool of pure samples or a chemical library e.g. prepared by combinatorial chemistry. The sample may comprise known and/or uncharacterised components. If a sample comprising uncharacterised compounds is found to contain a protein inhibitor, then the sample may be fractionated using standard techniques known in the art such as chromatography, (e.g. HPLC, thin-layer chromatography, FPLC, gel filtration, desalting etc.) and the resulting fractions or isolates may then serve as test samples in this assay. In this way it is possible to screen large pools of samples with relatively few assays, and additionally to screen samples that contain new or uncharacterised components without first purifying the components. It is also possible to administer pure samples to the assay. Thus the test sample may be any sample of pure or unpure material, provided in any convenient way e.g. it may be a test substance itself or it may be a composition containing a test substance (which test substance itself may be pure or unpure) and a carrier or diluent e.g. an appropriate medium. It may be a crude preparation or a purified or partially purified preparation.

The test sample may comprise synthetic or naturally occurring components. Naturally occurring components may for example be secreted by microorganisms such as bacteria or fungi, and provide a great range of chemical diversity. The test substance may thus be any substance that may enter the cell. It may thus be of any chemical nature including both complex and simple molecules, e.g. organic or inorganic molecules.

If the test substance enters cells inefficiently or is pumped out of the cell by efflux pumps, then the test cells may be modified to compensate for this. Permeable strains may be generated and used or the genes of known efflux pumps may be mutated and/or deleted, or functionally inactivated. This is performed using standard techniques.

The test sample may be applied to different aliquots of the cells in parallel or sequentially at a number of different concentrations. However preferably only a single concentration is required per test sample to ascertain whether a protein inhibitor is present, owing to the sensitivity of the screen.

The cell(s) used in the assay will preferably be a cell population, especially preferably a clonally derived population, the individual cells of which are genetically identical. The cell(s) will contain the two mutated genes (i.e. the first mutated gene carrying the lethal overactivity mutation and the second "compensatory" mutated gene). The mutations may be introduced into the genes, or the mutant genes may be introduced, in any convenient or desired way. The cells may have been transfected or transformed or transduced with the mutated genes, or the genes may have been introduced using other standard molecular biology techniques known in the art. The mutations alternatively may have been generated using standard mutagenesis (which may be directed or non-directed, e.g. random) and selection techniques e.g. by identification of revertants, suppressors or mutants. For example, cold sensitive suppressors of dnaA(ts) such as DnaACos may be identified by screening processes. For example, a temperature sensitive mutant cell, which contains a mutation in a protein such that the protein cannot function normally at the higher (restrictive) temperature could be used as the starting point. Suppressors may be generated, through normal processes or mutagenesis using standard techniques. If such mutants are e.g. cold sensitive, this property may in fact result from over-activity of the protein, rather than inactivity. In this way, it is possible to identify lethal overactivity mutants.

The cells may be any cells e.g. prokaryotic or eukaryotic cells, including eubacterial and Archael cells, as well as plant, fungal or animal cells, e.g. bacterial, mammalian or yeast cells (e.g. *Saccharomyces* sp. e.g. *S. cerevisiae* or *S. pombe*). Preferably, the cells are bacterial, more preferably the cells are *E. coli*.

In a most preferred embodiment, the cells (preferably bacterial cells) contain a lethal overactivity mutation in DnaA and a mutation which inactivates RNaseH (e.g. a deletion of rnh). A particularly preferred such mutant, DnaA219Δrnh, is described in the Examples herein identified as strain SF53 as deposited with the European Collection of Cell Cultures (ECACC), Porton Down, UK, on 6 May 2003 under accession number 03050701. The deposit was made in the name of The Norwegian Radium Hospital Research Foundation, of P.O. Box 56, Montebello, 0310 Oslo, Norway.

In another representative example, the lethal overactivity mutation is in the Cdc6 gene or in an Orc gene. Cdc6 and Orc are genes encoding replication initiator proteins in eukaryotes.

The term "mutation" as used herein refers to one or more changes in the nucleotide sequence of a gene. The change may represent the addition, deletion or substitution of nucleotides in the coding or non-coding regions of the gene and may affect the function of the gene product e.g. protein encoded by said gene or may affect the control of expression of said gene. For example the mutation may cause overexpression, i.e. an increase in expression levels when compared to a gene (e.g. a wild-type gene) that does not have this mutation. Alternatively, the mutation may lead to changes in the primary, secondary or tertiary structure of the protein product. Such changes may affect the function of the protein when compared to the non-mutated (e.g. wild-type) form of the protein. The changes in function may relate to increased activity caused by, e.g. altered binding of substrates or cofactors, altered mechanisms of regulation or localisation.

By "lethal overactivity mutation" it is meant that the genetic change or mutation as defined above causes an increase in the activity of the target protein, when compared to the non-mutated form of the protein i.e. the form of the protein as produced prior to or without the lethal overactivity mutation (e.g. as encoded by the wild-type gene) and this increase in activity decreases the viability of the cells containing the mutation.

The lethal overactivity mutation may be in any gene affecting the target protein, although generally it will be in the gene encoding the target protein. In addition to genes encoding a target protein a gene affecting the target protein may include any gene encoding a gene product which has an effect on the activity of the is target protein e.g. a regulatory molecule.

The increase in activity of the protein may result from an increase in protein expression, or from a structural or functional change in the protein (or its regulation), and may cause the growth rate of the cells containing the mutation to decrease or may cause the death of the cells. The mutation may affect the activity of any protein of the cell e.g. an enzyme or a structural protein, a receptor or signalling protein, or indeed any other functional or effector protein as long as the overactivity of this protein decreases cell growth and/or viability. The detectable phenotype of a cell containing such a lethal overactivity mutation (i.e. a lethal overactivity mutant) is therefore a reduction in the ability to grow, divide and/or survive.

As discussed above, the lethal overactivity mutation is preferably in a gene involved in DNA replication, more preferably in a gene involved in initiation of DNA replication, most preferably a gene involved in the initiation of prokaryotic and especially bacterial, DNA replication e.g. the dnaA gene. Mutations in the dnaA gene include dnaAcos and include the mutation dnaA219 of the *E. coli* initiation protein DnaA, as described herein in Example 1 below.

The preferred target protein is thus an initiator of DNA replication. Any initiator of DNA replication may be used, including from both prokaryotic (including archael) and eukaryotic sources. By initiator of DNA replication it is meant a protein that binds to the origin of replication, thus causing the process of DNA replication to start i.e. the protein is responsible for the first or initial step in the process of DNA replication. Eukaryotic replication initiator proteins include Cdc proteins (e.g. Cdc6, Cdc18 and Cdc45, Cdt proteins (e.g. Cdt1), Orc proteins (e.g. Orc1) and MCM proteins (Liu et al., 2000, Mol. Cell 6: 637). Homologues and orthologues of any such proteins (e.g. in other species) may also be used.

In eukaryotes replication starts with a six-subunit ORC complex bound at the origin, to which Cdc6, MCMs and Cdc45 are recruited. Archaea contain orthologues of several eukaryotic replication proteins, including Cdc6 and MCMs. Archaeal replication is thought to function analogously to that of eukaryotes, but with less complexity. Archae do not contain any obvious homologues of Orc, but Orc1 has homology to Cdc6, so it is thought that in archaea the "Cdc6/Orc" protein (i.e. the Cdc6 homologue) may play both roles. Cdc6/Orc from an archael species and DnaA have been crystallised recently and shown to be structurally similar proteins.

Whilst initiators of DNA replication are preferred as target proteins, as mentioned above any initiator protein may be used, i.e. any protein involved in the initiation of any cellular process e.g. transcription, or translation in the process of protein synthesis.

Mutant versions of such proteins which exhibit lethal overactivity may be generated and/or identified using standard procedures, as discussed above. In the case of certain proteins, appropriate mutants which may be used, are already known and have been described in the literature. These include mutants of DnaA (e.g. DnaAcos and DnaA219 mentioned above) and of Cdc proteins e.g. Cdc6 in yeast. Thus, for example, in the yeast *Saccharomyces cerevisiae*, mutants of cdc6 (cdc6-3 and cdc6-2) overreplicate even at permissive temperature and die at non-permissive temperature (Liang and Stillman, 1997, Genes Dev. 11:3375). In the yeast *Schizosaccharomyces pombe*, Cdc6 is called Cdc18. Cells that have overactivity of Cdc18, overreplicate (Nishitani and Nurse, 1995, Cell 83: 397; Muzi-Falconi et al., 1996, Proc. Natl. Acad. Sci. 93:1566).

The term "inducible" as used herein refers to the ability to switch the mutant phenotype of the cell containing the lethal overactivity mutant on and off. There are therefore two states—the non-induced state in which the cell is able to grow and divide normally, and the induced state in which this ability is compromised by the switching on of the mutation. This "inducibility" may be achieved in a number of ways. As one example, for a dominant lethal overactivity mutant, that is introduced into the cell in addition to the existence of a wild-type gene, and which has a dominant effect over the wild-type gene, in that the mutant phenotype is observed despite the presence of the wild-type gene, the mutant gene may be placed under the control of an inducible promoter. Similarly, whether it is dominant or not, where only the lethal overactivity mutant version of the gene is present (or is active) in the cell (e.g. where a "normal" or wild-type gene is absent or has been inactivated e.g. knocked-out), an inducible promoter may be used. This promoter requires the presence of a certain component (i.e. effector) in the growth medium for transcription of the gene that has been artificially placed under its control to occur. In this way, no transcription of the mutant gene (e.g. exogenous mutant gene) occurs in the absence of this component (effector) and thus no mutant protein is produced. In the presence of the component/effector, the mutated gene is transcribed and mutated protein is therefore produced. If the lethal overactivity mutant is dominant, its presence will affect cell viability, even in the presence of the "non-mutated" (e.g. wild-type) protein. In the absence of the "non-mutated" protein (or in the absence of its activity) the effect of any lethal overactivity mutation will likewise be observed. For example, the mutant gene may be placed under the control of the lac promoter, the λ promoter or the arabinose promoter.

Alternatively, the mutant phenotype of the protein may be induced by conditional means, i.e. the lethal overactivity mutation may be a conditional mutation, wherein the mutant phenotype of the target protein is induced by a change in one or more conditions (e.g. parameters) pertaining to the cell (e.g. temperature or other culture conditions, age, nutrition). Restrictive conditions are those in which the mutant phenotype is observed, whereas permissive conditions are those in which the mutant phenotype is suppressed (e.g. resulting in non-overactive gene function e.g. wild-type or normal activity levels) (i.e. "non-mutated") gene function. Thus the mutant phenotype of the mutant protein may be induced by a change in the temperature of the cell. Temperature or cold sensitive mutations are widely known in the art and result from changes in the primary structure (i.e. the amino acid sequence) of the mutated protein. Certain amino acids at key positions in the protein may confer temperature sensitivity. The secondary structure of the protein changes following a shift in the growth temperature of the cell containing the mutated protein.

The changes in the conformation of the protein at different temperatures may result in changes in the properties of the protein. For example, the protein may become excessively active at one temperature, whilst behaving essentially in the normal, wild-type manner at another temperature. Alternatively, the protein may function normally i.e. with wild-type activity levels at one temperature and be rendered inactive or have reduced activity by the change in temperature. The temperature at which the protein behaves normally is termed the permissive temperature. The temperature at which the protein displays the mutant properties e.g. reduced, increased or different activity is termed the restrictive temperature.

These temperature sensitive or cold sensitive mutants have proved very useful to study the effects of lethal mutations. Growth and propagation of the cell or organism at the permissive temperature allows the expansion and perpetuation of cells harbouring proteins with the mutations in question. By subjecting the cells to the temperature shift, and thus revealing the mutant phenotype, it is possible to study the function of otherwise lethal mutations. Temperature and cold sensitive mutations are advantageous as the change in protein structure and function occurs on the temperature shift, and does not have a lag phase as may be seen when other inducible systems are used, for example the addition of an inducer of transcription. It is thus preferred that the lethal overactivity mutants of the invention are temperature or cold sensitive. It is most preferred that the restrictive temperature is 30° C. and the permissive temperature is 42° C.

By "target protein" is meant a protein which has been identified as being essential or crucial to the growth and/or survival of the cell in which it is contained or expressed, and for which it is desired to identify an inhibitor, e.g. for use as a candidate drug against the target protein. Thus for example the target protein may be crucial or essential to a pathogen, or to the continued existence of a disease state. As mentioned above certain proteins may be associated with particular disease conditions e.g. cancer, and may thus represent potential drug targets. As also discussed above, drugs that interfere with these target proteins may be identified in screens whereby the effect of a potential drug on the target protein is measured via the effect of the drug on the phenotype of a cell that requires said target protein for its growth and/or survival.

According to the invention, the target protein is mutated such that it is a lethal overactive mutation, i.e. it has increased or excessive activity when compared to the non-mutated or wild-type protein. In this way, it is the reduction in the mutant overactivity of the target protein, which is assessed in the assay. This provides a positive assay in that the reduction in activity of the mutant lethal overactive protein is detected. If the cells containing the mutant overactive protein survive, then it can be seen that the test substance comprises a compound which reduces the overactivity of the mutated target protein. Such a compound has potential for use as a drug to interfere with the normal activity of the target protein, and to thereby reduce infection or to combat the disease state in question.

As mentioned above, The target protein may be any functional protein, (e.g. any effector protein) but it is preferably an enzyme or a binding protein, particularly an enzyme or binding protein that is involved in the metabolism of DNA. Especially preferred is a protein that is involved in the replication of chromosomal DNA, such as bacterial (e.g. *E. coli*) DnaA or a homologue thereof. Homologues of DnaA may be found in other species such as *E. coli, S. enterica, S. marcescens, P. mirabilis, B. aphidicola, Y. pestis, V. harveyi, V. cholerae, P. putida, P. aeruginosa, P. multocida, H. influenzae, S. putrefaciens, C. crescentus, R. meliloti, Z. mobilis, R. prowazekii,*

*Wolbachia* sp., *H. pylori, C. jejuni, B. pertussis, N. meningitidis, T. ferrooxidans, C. difficile, B. subtilis, B. halodurans, B. anthracis, S. aureaus, S. pneumoniae, M. capricolum, M. genitalium, M. pneumoniae, U. urealyticum, S. citri, E. faecalis, M. luteus, C. diphtheriae, M. leprae, M. avium, M. tuberculosis, M. smegmatis, S. coelocolor, S. chrysomallus, P. marinus, Synechocystis* sp., *C. pneumoniae, C. trachomatis, C. muridarum, B. burgdorferi, T. pallidum, T. denticola, T. maritima, T. thermophilus, D. radiodurans, A. aeolicus, C. tepidum, D. ethenogenes, P. gingivalis*. Other proteins involved in DNA replication may also be used e.g. the eukaryotic Cdc6/Orc proteins mentioned above or any other replication initiators.

The mutation in the second gene is required to enable the detection of strong protein inhibitors, which would not usually be detected in the case of a simple positive screen. In a normal, single mutant, positive screen where a cell comprising a single lethal overactivity mutant is used, a protein inhibitor that compromises the activity of the overactive mutant such that the activity is reduced, but not completely abrogated, may cause the cell to survive, or to show increased survival or growth in the presence of such an inhibitor when compared to the mutant cells grown in the absence of such an inhibitor. However if a strong inhibitor, which substantially or completely abrogates the function of the lethal overactivity mutant is present (e.g. in the test sample) then the mutant cells will die, irrespective of the presence of such an inhibitor. By its nature, the target protein that contains the lethal overactivity mutation, is essential to the continued survival and/or growth and propagation of the cell and it is for this reason that it makes a suitable target protein, and via this property that inhibition of the target protein is measured. However it is not possible in such a system to differentiate between a strong inhibitor, which prevents survival of cells containing the lethal overactive mutant by completely or significantly inhibiting the activity of the mutated target protein, which is essential to the continued survival of this cell, and the absence of any inhibition, in which conditions the cells cannot survive. Thus, any positive screen which utilises a single, lethal overactivity mutation is limited with respect to the strength of inhibitions that may be detected in said screen, in that only weak inhibitors, or stronger inhibitors used only in low amounts, are detected.

The inventors have developed a new assay in which a second mutation that is also present in the cell, enables the cell to survive if the protein inhibitor is sufficiently strong (or present in sufficiently high amounts) to completely abrogate the function of the target protein, or to reduce it to a level below that at which the cell can survive and/or grow.

The second mutation substitutes and compensates for the lack of activity of the target protein caused by any reduction in activity by the protein inhibitor and its phenotype is therefore only detectable when the activity of the first lethal overactivity mutant is reduced, as the lethal overactivity mutant is dominant. The second mutation may be the insertion of a new gene or genes, the product(s) of which may function to compensate for the lack of activity of the target protein. Alternatively, the mutation may be a mutation which inactivates a particular gene/gene product or substantially reduces its expression and/or activity e.g. a nonsense mutation in a gene or deletion which removes the product or the functional product of the gene from the cell.

The mutation in the second gene allows the continued survival and growth of the cell in the presence of a strong inhibitor (or of high concentrations or amounts of inhibitor), that reduces the activity of the target protein. The mutation in the second gene thus may act at the same level or downstream of the lethal overactivity mutant. So, where the lethal overactivity mutation is in an initiator of a cellular process, the second mutation allows this process to proceed in the absence of any functional initiator of this process. For example, where the lethal overactivity mutant is in an initiator of DNA replication e.g. in prokaryotes and results in an overactive DNA replication initiator protein (e.g. DnaA), causing overinitiation of DNA replication, the second mutation preferably is one that allows DNA replication to proceed in the absence of the functional DNA replication initiator protein (e.g. DnaA), e.g. by providing an alternative mechanism of replication. Thus for example, said mutation may be any mutation that inactivates the rnh gene encoding RNase H and is most preferably the deletion of rnh.

By "functionally compensates" it is meant that a further or alternative activity is introduced or deleted (or substantially reduced) in the mutant cell. The compensation thus lies in providing a means by which the cell may continue to function essentially normally, despite the absence or reduction of the activity of a key target protein. The second mutation may thus functionally compensate for any reduction in the activity of the first gene product (i.e. the target protein), below a viability-sustaining level (i.e. if the activity of the target protein falls below a level at which the cell can survive and/or grow. The activity of the target protein is not measured directly and is measured in a functional assay.

For example in a linear signalling pathway, the target protein may be "upstream" of the alternative activity. By providing an active protein downstream of the blocked activity, the signalling pathway continues to function and the cell that is dependent on this pathway will survive in the absence of a functional upstream signal. The alternative activity may therefore be downstream or act at a later point in a signalling pathway.

"Degree of survival" as used herein refers to the assessment (e.g. measurement) of the growth and proliferation of the cells used in the assay. The cells will be killed (or will be unable to grow) by the lethal overactivity mutation, when this is induced, in the absence of a protein inhibitor which will inhibit the effect of the target protein. This therefore represents a degree of survival of "zero", i.e. no cells survive, or no cells are able to grow and divide. Following induction of the lethal overactivity mutation, it may take a certain period of time for the cells to die. For example, it usually takes approximately 3 hours following the induction of a temperature sensitive lethally over-active mutation in bacteria for the cells to die. In the presence of a specific protein inhibitor that reduces the activity of the lethal overactivity mutant, an increased number of cells will survive and may proliferate. Thus the degree of survival correlates with the number of cells present (e.g. in the cell growth or culture medium) following the induction of the lethal overactivity mutation and the addition of the inhibitor (or test sample). The inhibitor (or test sample) may be added simultaneously with the induction of the lethal overactivity mutation or subsequently. If the induction of the lethal overactivity mutation occurs via a temperature shift then it is preferable that the inhibitor (or test sample) is added simultaneously with the induction of the lethal overactivity mutation. If the induction of the lethal overactivity mutation requires de novo protein synthesis then the inhibitor (or test sample) should be added subsequently to the induction of the lethal overactivity mutation, preferably at a time where protein synthesis has occurred e.g. 3-5 hours or 5-8 hours following the induction of the lethal overactivity mutation.

This may be performed by determining e.g. by estimating or assessing (e.g. by counting or measuring) the number of cells (e.g. live cells) at a defined time point in the presence and absence of test sample. Cells may be enumerated spectrophotometrically e.g. by measuring the optical density of the cell population at an appropriate wavelength, e.g. a wavelength of 450 nm or by directly counting the cells, or a representative proportion of the cell sample. If the cells are grown on solid medium, the colony number may be determined.

As mentioned above, if the induction of the lethal overactivity mutation occurs in a temperature shift, the inhibitor or test sample should be contacted with the cells shortly after e.g. 1 generation or simultaneously with the induction of the lethal overactivity mutation. This represents time zero. The determination of the relative numbers of cells may then be performed at appropriate time intervals e.g. 3-30, 5-30, 5-25, 5-20, 5-15, 5-12, 5-10, 8-12, 8-10, 3-5 generations after time zero, or after an appropriate incubation period, e.g. overnight incubation of 8-30 hours, 8-24 hours, 8-18 hours, 8-12 hours, 12-30 hours, 12-24 hours, 12-18 hours, 18-30 hours, 18-24 hours, 20-30 hours, 20-24 hours. At this time, the number of cells in the induced cell population in the absence of test substance is the control value. The number of cells in this cell population is compared to the number of cells in the induced cell population that has been contacted with the inhibitor/test sample. For example, an increase in the $OD_{450}$ of 10 times, 20 times, 30 times, 50 times or 100 times, relative to the value in the absence of the inhibitor/test sample indicates the presence of a protein inhibitor in the test substance.

In a further aspect, the invention relates to cells for use in the method of the invention. Such a cell contains an inducible, preferably temperature e.g. cold sensitive, lethal overactivity mutation in a first gene affecting (e.g. encoding) a target protein, the activity of which is essential to the cell, and a second mutation (e.g. in a second gene) that functionally compensates for any reduction of activity of the first gene product (i.e. of the target protein), for example a reduction of activity caused by a protein inhibitor.

As mentioned above, the cell may be eukaryotic or prokaryotic including Archael cells, e.g. yeast, or mammalian cells. Preferably the cell is eubacterial, e.g. *E. coli*.

More preferably the cell is a dnaA219Δrnh mutant, preferably derived from strain WM2667, and most preferably the cell is deposited strain SF53 as defined above, containing the DnaA219cosΔrnh mutation, with the characteristics set out in Table 1.

A further aspect of the invention relates to a kit for performing the assay, comprising cells for performing the assay. The kit may also comprise growth medium and/or antibiotics for performing the assay.

A still further aspect of the invention extends to protein inhibitors (e.g. novel protein inhibitors) identified by the assay method of the invention, particularly inhibitors of DNA replication, especially inhibitors of bacterial DNA replication, and their use as antimicrobial agents.

BRIEF DESCRIPTION OF THE DRAWINGS

The invention will now be described in more detail in the following non-limiting Examples with reference to the drawings in which.

DETAILED DESCRIPTION OF THE PREFERRED EMBODIMENT

EXAMPLES

Example 1

Construction of Test Strain SF53

WM2667 is a temperature sensitive suppressor of WM2062 (dnaAtS46, Weigel et al., 1999, Mol. Microbial, 34: 53-66). WM2667 closely resembles the dnaAcos mutant (Kellenberger-Gujer et al., supra) in that it is a cold sensitive mutant of dnaA. The mutants grow normally at the permissive temperature (42° C.), however after growth at the restrictive temperature, 30° C. for 4 hours, less than 10% of the cells remain viable. At 30° C., the cells accumulate 3-4× more OriC DNA than control markers (dnaB, dnac and attλ). Growth may be restored by introduction of an OriC plasmid or moderate overexpression of the Fis protein.

There are three mutations present in the dnaA gene of WM2667; A184V and H252Y are both present in the dnaA gene of the parental strain, whereas R342C represents an additional mutation only found in WM2667. The dnaA allele is termed dnaA219(cos).

In order to construct a strain that could survive the condition where the DnaA219 protein is completely inactivated, deletion of the rnhA gene was introduced into strain WM2667 by P1 transduction according to standard procedure (Miller et al. (1992), A short course in bacterial genetics: A laboratory manual and handbook for *E. coli* and related bacteria (Cold Spring Harbour Press)).

P1 Lysate of Strain SS198:

An overnight culture of SS198 (rnh::cam) was diluted 1:100 in 10 ml LB+chloramphenicol and grown to OD=0.3. $CaCl_2$ was added to 10 mM and incubated at room temperature for 5 minutes. 100 μl P1 stock was added and incubated at room temperature for 15 minutes. The incubation was continued at 37° C. with shaking for 4 hours. 1 ml chloroform was added and incubated at 37° C. for 15 minutes. The tube was spun, the supernatant transferred to a new tube.

Transduction of rnh::cam to WM2667:

15 mM of $CaCl_2$ and 15 mM $MgCl_2$ was added to an overnight culture of strain WM2667 and incubated at room temperature for 15 minutes. 500 µl P1 lysate was added to 1 ml overnight culture and incubated at 37° C. for 15 minutes.

The tube was spun and the culture washed LB+50 mM Na-citrate. The culture was resuspended in 150 µl LB+50 mM Na-citrate, and incubated at 37° C. for 1 hour. All the culture was plated on LB plates with appropriate antibiotics.

The resulting strain, SF53 (dnaA219 rnh::Cam) lacks the RNase H protein. This strain grows normally at 42° C. but does not survive at 30° C. Otherwise, it has the same genotype as WM 2667.

Strain SF53 does not survive at 30° C. To investigate the frequency of reversion from cold sensitivity the following experiment was performed. An overnight culture of SF53 grown at 42° C. was diluted 1:1000 in fresh $ABB_1$ glucose CAA medium and growth continued at 42° C. until the $OD_{450}$ reached about 0.15 (i.e. about 4 generations). The doubling time of the culture was about 90 minutes. Several different dilutions of the strain were plated on $ABB_1$ glucose CAA plates and the plates incubated at either 30° C. or 42° C. Colonies were counted after 18, 24 and 42 hours. The plates that had been incubated at 42° C. showed about $10^7$ colonies per ml culture plated and indicate that 1 ml culture of SF53 with an $OD_{450}$ of 0.1 contains $10^7$ viable cells. The plates incubated at 30° C. for 18 and 24 hours showed about 10 colonies per 1 ml culture plated. This means that 1 cell per $10^6$ was no longer cold sensitive. The plates that were incubated for 42 hours had a 5 to 10 fold increase in the number of cold resistant colonies, showing that prolonged incubation picks up a higher number of revertants.

Example 2

Survival of Strain SF53 in the Absence of DnaA Activity

The following experiments were performed to provide evidence that strain SF53 will survive when a drug has inactivated the DnaA protein. Such evidence can be obtained without a lead drug, by using production of the N-terminal domain (Domain I amino acids 1 to 86) of wild type DnaA. Domain I of DnaA is important for oligomerization and formation of proper initiation complexes. If independent Domain I is synthesized, inactive hetero-oligomers of DnaA and Domain I will be formed, thus leading to a "poisoning" of the initiation complexes. Strain SF53 was transformed with a plasmid carrying an IPTG-inducible gene encoding biotin-tagged Domain I (pBEX5BA-dnaA[1-86]-biotin), transformants checked, and the strain named SF58 (Table 1).

TABLE 1

Strains

| Strain | Genotype | Reference |
|---|---|---|
| WM2667 | argE3, del(lac-pro), dnaA219(Cos), galK2, his-4, lacY1, lambda-, leuB6, mtl-1, rpsL31, supE44, thi-1, tsx-33, xyl-5 (derivative of AB1157) | (Weigel et al., 1999) |
| SF53 | WM2667rnh::Cam | this work |
| SF58 | SF53/pBEX5BA-dnaA[1-86]-biotin | this work, (Weigel et al., 1999) |

Figure 1:
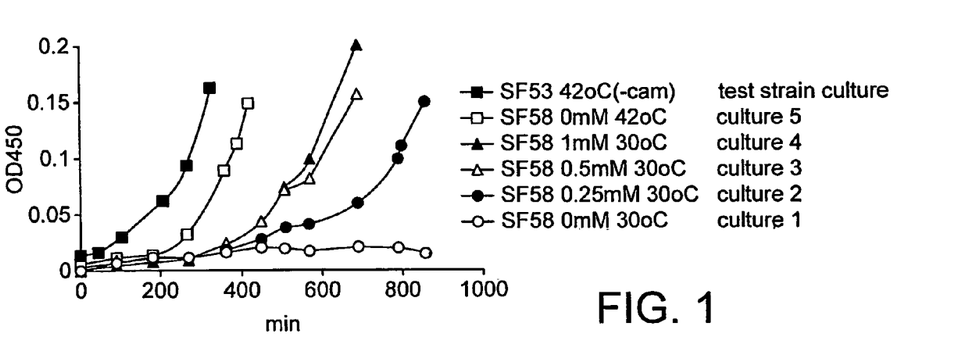
FIG. 1 shows growth curves of test strain SF53 (dnaA219, rnh::cam) and strain SF58 (dnaA219, rnh::cam/pdnaA[1-86]-biotin)

The growth of strain SF58 was tested at three different concentrations of IPTG. An overnight culture of strain SF58 grown at 42° C. was diluted 1:1000 in fresh $ABB_1$ glucose CAA medium and split into five flasks. Culture nos. 1 to 4 were grown at 30° C. and culture no. 5 at 42° C. IPTG was added to culture no. 2, 3 and 4 at a concentration of 0.25, 0.5 and 1 mM, respectively, at the time of dilution. Growth curves were followed by measurement of $OD_{450}$ for 8 hours. The experiment shows that culture no. 1 grown at 30° C. without IPTG did not survive (FIG. 1). The $OD_{450}$ was less than 0.03 at all time points. This result confirms that the dnaA219rnh strain does not survive at 30° C.

The control culture (no. 5) grown at 42° C. had a doubling time of about 60 min. The three cultures grown at 30° C. with IPTG showed increasing growth rates with increasing concentration of IPTG and hence having concentrations of domain I protein (see below). This result shows that growth of the strain at 30° C. was restored by induction of Domain I, and that the growth rate improved with increasing amounts of Domain I.

The concentrations of Domain I present after 4 generations growth in the presence of the three different concentrations of IPTG, was assessed by Western blot. A ten-fold difference in $OD_{450}$ between the culture grown without IPTG (culture no. 1) and the culture grown with 1 mM IPTG (culture no. 4) was obtained after about 10 hours. Thus, when performing a drug screen with the dnaA219rnh strain, a positive hit will be detected by a ten-fold difference in $OD_{450}$ after about 10 hours in the presence of the drug.

Figure 2:
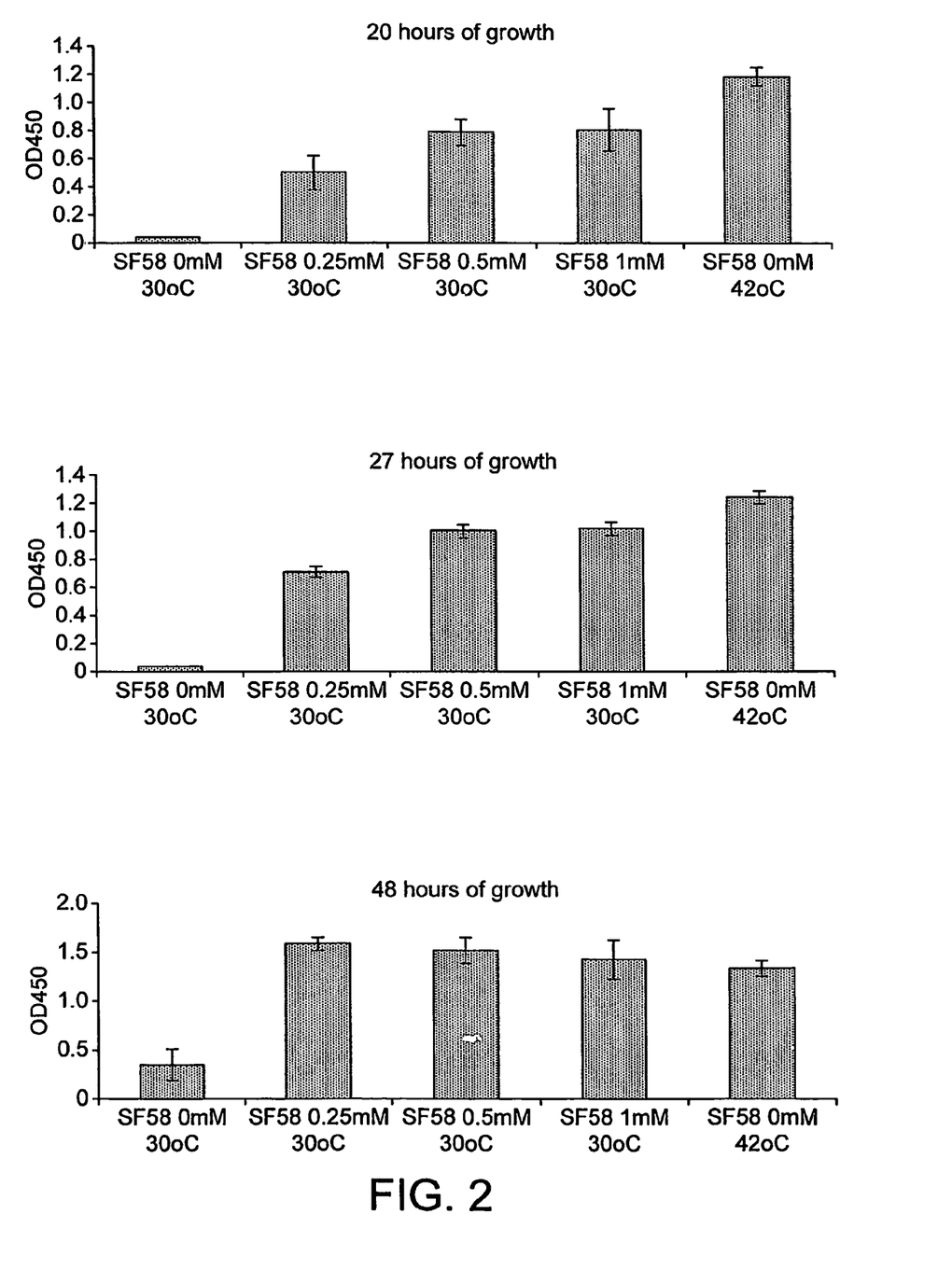
FIG. 2 shows analysis of viability of SF58 cells grown with different amounts of IPTG (0, 0.25, 0.5 and 1 mM) at 30° C.

To determine the robustness of the screen and also at which time, in a high throughput assay, it is optimal to measure the difference in $OD_{450}$ we made the following measurements (FIG. 2). Essentially the same experiment as in FIG. 1 was performed, but $OD_{450}$ was measured at only three time points, 20 h, 27 h and 48 h, in 10 different parallel cultures. A 20-40 fold difference was obtained after 20 h and after 27 h. After 48 h a background in the uninduced culture started to appear and the difference dropped to about 5 fold. Therefore, measurements of $OD_{450}$ in high throughput screens should be performed after 10-30 hours of incubation.

Example 3

High Throughput Screening Procedure

An overnight culture of strain SF53 grown in $ABB_1$ glucose CAA medium at 42° C. is diluted 1:1000 in fresh medium and distributed into an appropriate number of 96-well microtiter plates. Different test substances are added, one to each microtiter well, except for two of the wells in each plate. These two serve as blanks, i.e. reference cultures with no growth. The microtiter plates are incubated at 30° C. for 20-24 h, then OD450 is measured. Positive hits are found in wells with OD measurements 10-100 fold higher than that of the blank samples.

Example 4

Validation of Assay

Figure 3:
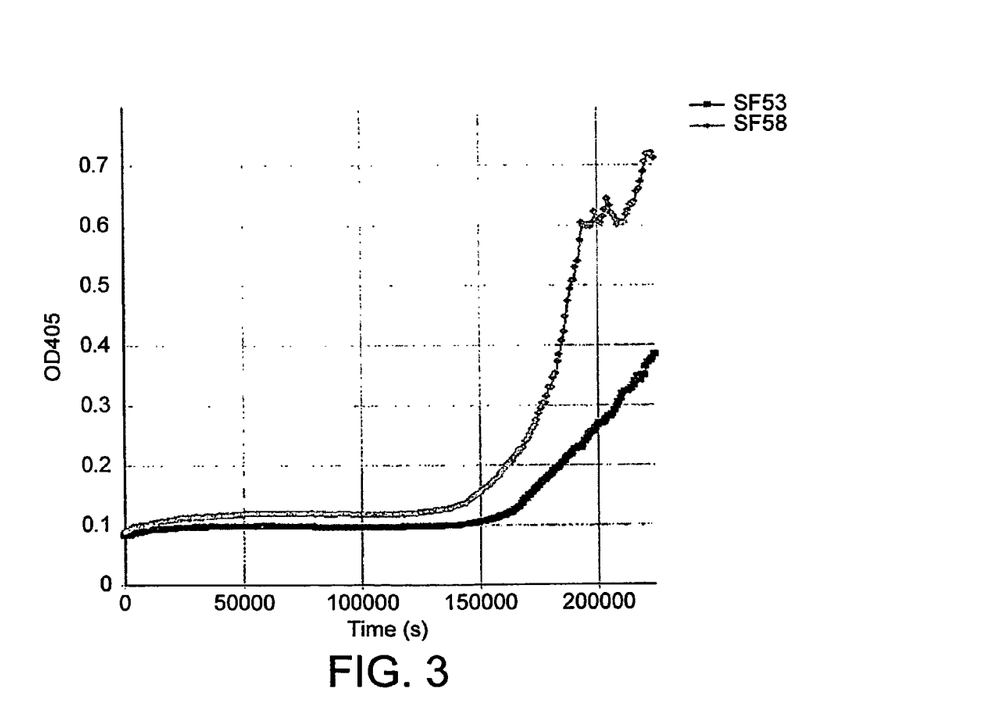
FIG. 3 shows the growth curves of SF53 and SF58. The inoculum was a 1:100 dilution of 1.5 $OD_{600}$ O.N. culture. Incubation temperature was 30° C., $OD_{405}$ was measured every 900 s. Neither SF53 nor SF58 show any appreciable growth in these conditions up to $1.5 \times 10^5$ s (approximately 42 h)
Figure 4:
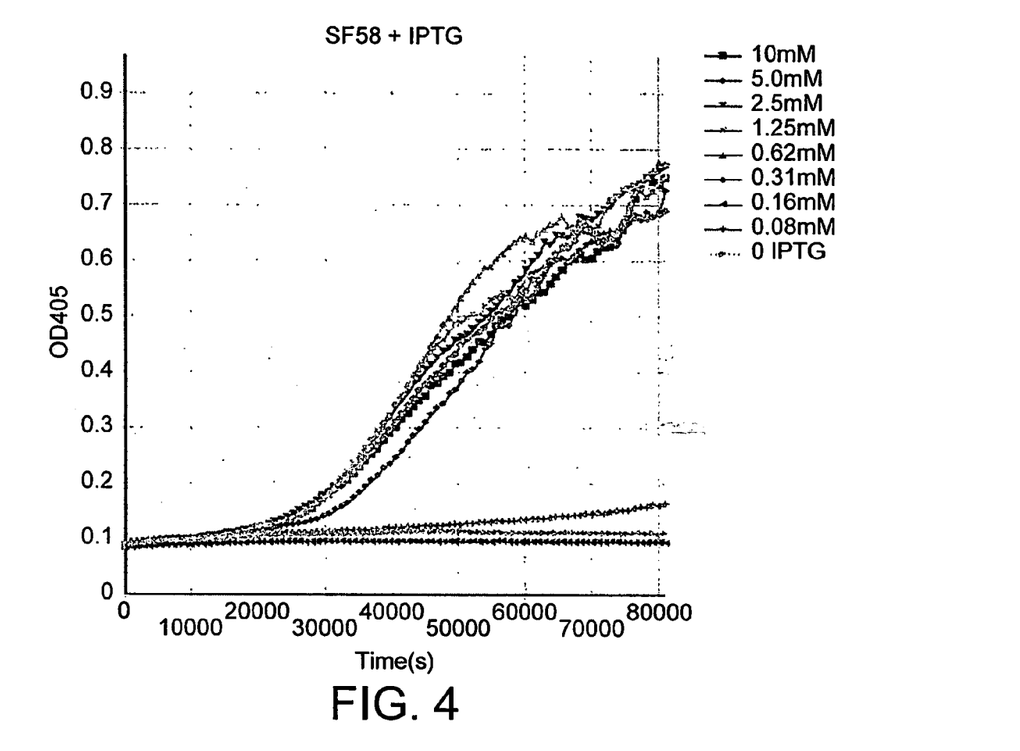
FIG. 4 shows the growth curve of SF58 with IPTG at concentrations of 0 to 10 mM. The inoculum was a 1:100 dilution of 1.5 $OD_{600}$ overnight culture. Incubation temperature was 30° C., $OD_{405}$ was measured every 900 s. After 18 hours. ($6.4 \times 10^4$ s) the ODs of the induced cultures (0.31 mM IPTG and above) are significantly higher than controls (0 to 0.16 mM IPTG)

The first part of an assay transfer & validation procedure involves the reproduction of the results in microtiter format. These results are shown in FIG. 3, which indicates that neither SF53 nor SF58 shows any appreciable growth when incubated in microtiter format at 30° C. for up to $1.5 \times 10^5$ s (approximately 42 h). All 48 replicate cultures of the same microtiter plate of FIG. 3 behaved similarly. Next, the IPTG induction curves were reproduced, as shown in FIG. 4. SF58 can show an $OD_{405}$ significantly higher than control already after $3 \times 10^4$ s (approximately 8 h). In addition, after 18 h ($6.4 \times 10^4$ s) the OD's of the induced cultures are well above controls. These results confirm the expected behaviour of strains SF53 and SF58-IPTG, and indicate that there is a wide temporal window during which the effect of a hypothetical DnaA inhibitor can be unambiguously measured.

A series of experiments were then performed to assess the signal as a function of the starting inoculum (i.e. the theoretical OD of the culture present in a microtiter well). The data (not shown) indicate that there is no significant difference in the SF58-IPTG growth curve if the inoculum is obtained by dilution of an overnight culture or of an actively growing 42° C.-culture. Consequently, the time for measuring the OD was set at 18 h, and the procedure used was to grow 5 µl of SF53 or SF58 in 30 ml glucose CAA medium (with antibody selection) overnight at 42° C. until the $OD_{600}$ was 1.2. The stock was diluted 1:100 in glucose CAA (without antibody). 90 µl of this was dispensed into each well, with 10 µl of sample. $OD_{620}$ was measured after an 18 hour incubation at 30° C.

Since there are no known small molecule inhibitors of DnaA, the next step to validate the assay was to register assay performance in the presence of unknown samples. To this end, we made use of the microbial extracts library present at Vicuron Pharmaceuticals. It should be noted that this library consists of processed microbial fermentation extracts. Briefly, each strain is fermented under defined conditions, and the fermentation broth is processed by solid-phase extraction and the cells are processed by solvent extraction. In either case, the "microbial extract" is dispensed into microtiter plates and dried. Microbial extracts are stored in 96-well microtiter plates at 80 samples per plate. The remaining 16 wells per plate are used for positive and negative controls. Each sample in the library of microbial extracts therefore consists of a mixture of unknown compounds at unknown concentrations. Evaluating the assay performance with such a complex library of samples has the potential to highlight any possible interference and poor test performance.

The assay should identify the presence of a DnaA inhibitor as a sample giving a $OD_{620}$ significantly higher than controls. From a theoretical point of view, we would expect true positives to be relatively rare, since they should contain such an inhibitor at a concentration sufficient to allow growth of SF53. In addition, we can theoretically identify two groups of false positives: one group could arise from all those cases in which the appearance of a significant $OD_{620}$ does not depend on SF53 growth (i.e. a contaminating microbe or a turbid sample generates the signal); another group could arise from all those cases in which the particular well contains a high number of suppressor strains. Both groups of false positives can be easily recognized by test repetition with or without SF53. Considering the nature of the samples, possible false negatives could consist of all those samples in which a hypothetical DnaA inhibitor is present together with another antibiotic active on SF53. However, we know that the frequency of microbial extracts active against an *E. coli* strain is around 1%, so false negatives should be quite rare.

Following the procedure outlined above, a screening of 4240 microbial extracts was performed. Each 96-microtiter plate contained as controls four wells inoculated with SF53, four wells inoculated with SF58 and 8 wells inoculated with SF58 in the presence of 2.5 mM IPTG. 10 µl of 10% DMSO (the solvent in which the microbial extracts are dissolved) was added to these control wells.

Figure 5:
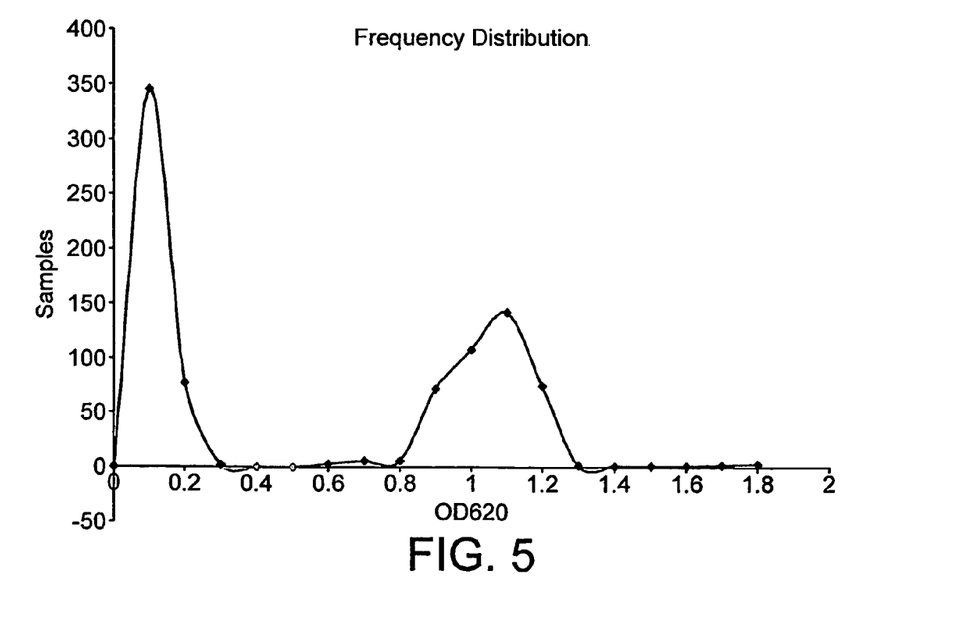
FIG. 5 shows the Frequency Distribution of $OD_{620}$ value of positive (SF58+2.5 mM IPTG) and negative (SF53 and SF58) controls. The positive control values are grouped around $OD_{620}$ 1.1 and negative control values are grouped around $OD_{620}$ 0.1.

We can first observed the frequency distribution of the controls, as reported in FIG. 5. All negative controls (SF53 and SF58) group around 0.1 $OD_{620}$, while the positive controls (SF58-IPTG) show a broad distribution curve around 1.1 $OD_{620}$. A broad distribution curve for positive controls as in FIG. 5 is not ideal in a screening program. However, it could be due to the manual dispensing of the inoculum, and it should improve upon automation of inoculum dispensing. Nonetheless, there is a clear separation between negative and positive controls, and this should allow the unambiguous identification of positive samples.

Figure 6:
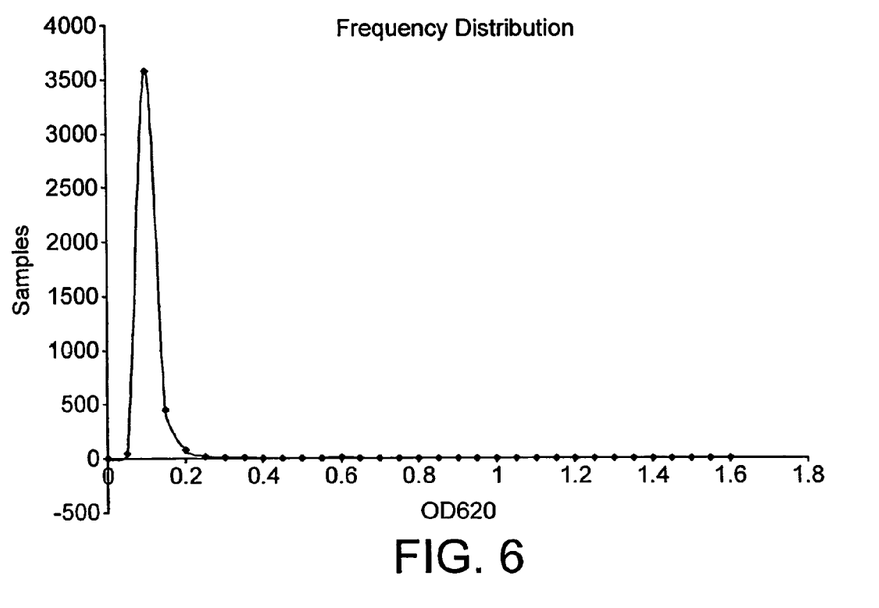
FIG. 6 shows the Frequency Distribution of $OD_{620}$ value of 4240 Microbial extracts. Most samples have an $OD_{620}$ around 0.1.
Figure 7:
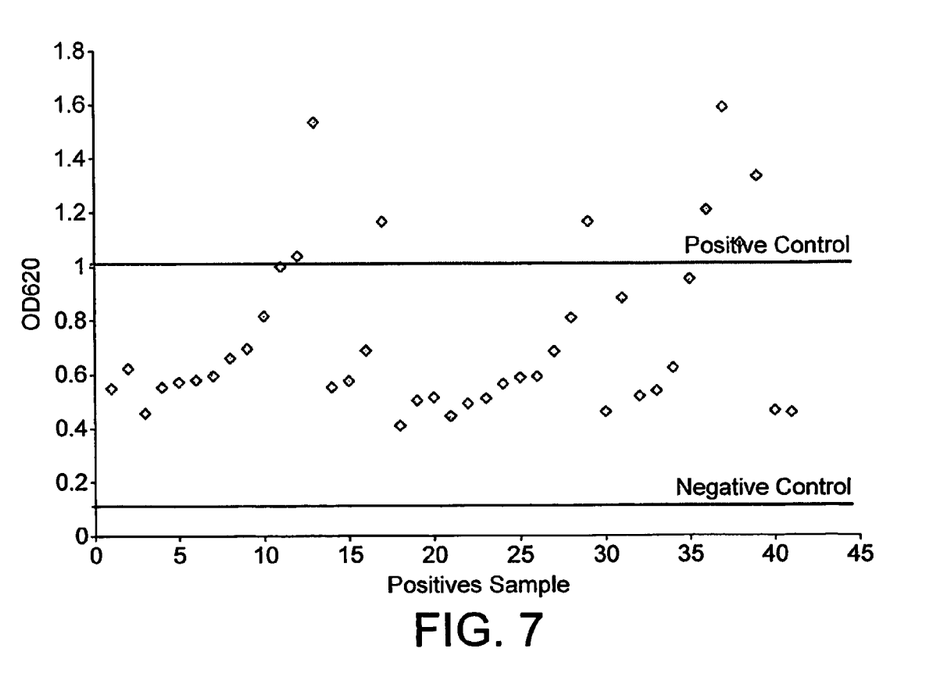
FIG. 7 shows the $OD_{620}$ signal from the 41 positive Microbial extracts.

The frequency distribution of the 4240 microbial extracts is shown in FIG. 6. It can be seen that most samples cluster around 0.1 $OD_{620}$. This indicates that most samples do not result in an $OD_{620}$ significantly different from that of the negative controls. In addition, this frequency distribution indicates that a threshold of 0.4 $OD_{620}$ could be used to identify true positive samples. This cutoff identified 41 samples (representing 0.97% of the tested samples) with an $OD_{620}$ higher than 0.4. The observed values for these positive samples are reported in FIG. 7. These results were subsequently shown to be false positives due to the presence of microbial contamination from the extracts used as the samples. This contamination may be tested for readily, using standard microbiological techniques.

At this stage, we can conclude that:
a) the assay can be performed in 96-well format;
b) it performs adequately for a HTS program;
c) the positive microbial extracts are all false positives.

What is claimed is:

1. A method for identifying the presence of an inhibitor of DnaA in a sample, comprising the steps of:
   a) contacting said sample with a bacterial cell, wherein said cell contains
      i) an inducible lethal overactivity mutation in a gene encoding DnaA; and
      ii) a mutation in a second gene encoding RNase H, wherein the mutation inactivates RNase H;
   b) inducing the lethal overactivity mutation; and subsequently
   c) assessing protein inhibition by comparing the degree of survival of the cell in the presence and the absence of said sample,
wherein the cell is DnaA219Δrnh, deposited with the ECACC under Accession No. 03050701.

2. *E. coli* strain SF53 (DnaA219αrnh), deposited with the ECACC under Accession No. 03050701.

* * * * *